United States Patent [19]

Taylor

[11] Patent Number: 5,574,277

[45] Date of Patent: Nov. 12, 1996

[54] INTRODUCTION OF SAMPLES INTO AN ION MOBILITY SPECTROMETER

[75] Inventor: Stephen J. Taylor, Buckinghamshire, Great Britain

[73] Assignee: Graseby Dynamics Limited, Bushney, Great Britain

[21] Appl. No.: 182,010

[22] PCT Filed: Jul. 27, 1992

[86] PCT No.: PCT/GB92/01388

§ 371 Date: Jan. 24, 1994

§ 102(e) Date: Jan. 24, 1994

[87] PCT Pub. No.: WO93/03360

PCT Pub. Date: Feb. 18, 1993

[30] Foreign Application Priority Data

Jul. 26, 1991 [GB] United Kingdom ............ 9116222.2

[51] Int. Cl.⁶ ................................................. H01J 49/40

[52] U.S. Cl. ............................................ 250/281; 250/288

[58] Field of Search .................................. 250/282, 288, 250/281, 282, 288 A

[56] References Cited

U.S. PATENT DOCUMENTS 4,551,624  11/1985  Spangler et al. ................ 250/287
5,021,654  6/1991   Campbell et al. ................ 250/287
5,283,199  2/1994   Bacon, Jr. et al. ............... 250/287

Primary Examiner—Jack I. Berman
Attorney, Agent, or Firm—Robert A. Schruhl

[57] ABSTRACT

In the type of ion mobility spectrometer having a unidirectional drift and source flow (30) which is exhausted (22) downstream of an ionisation source (10), improved sensitivity is obtained by entraining the effluent (18) from a gas chromatograph within a faster moving further gas flow (32), both being introduced in a direction counter to that of the said unidirectional flow.

5 Claims, 1 Drawing Sheet

INTRODUCTION OF SAMPLES INTO AN ION MOBILITY SPECTROMETER

BACKGROUND OF THE INVENTIONS

The present invention relates to ion mobility spectrometers (IMS's) and more particularly to a method and apparatus for introducing the effluent from a gas chromatograph into an ion mobility spectrometer.

The use of an ion mobility spectrometer in combination with a gas chromatograph employing, for example, a capillary on a packed separating column, is a well established technique.

SUMMARY OF THE INVENTION

FIG. 1 of the drawings attached show diagrammatically such a combination and the various gas flows in prior art equipment of this type.

An ion mobility spectrometer with an ionising source 10, a gating grid or grids 12, drift field electrodes 14 and a collector electrode 16, is linked with the outlet 18 of, for example, a capillary column gas chromatograph (not shown).

Time separated components of a sample introduced into the gas chromatograph appear at the outlet 18, are fed, together with the gas chromatograph carrier gas flow, into the ion mobility spectrometer in the region of the source 10, and are ionised. Sample ions and any unionised molecules are swept by the source gas flow 20, introduced through a port 22, into the region of the gating grids 12, which permit ions to enter the drift tube 13. Ions not passed by the grids 12, together with un-ionised molecules and chromatograph carrier gas, are swept out of the gating grid region through the exhaust vent 24.

Ions entering the drift tube 13 pass to the collector electrode 16 through the electric field set up by the electrodes 14, against the flow of the drift gas 26, introduced through a port 28, which sweeps out via the exhaust vent 24 any ions failing to reach the collector electrode 16.

The time of arrival of ions at the collector 16 is indicative of the identity of their parent molecules and the magnitude of the collector current flow produced by any group of ions is an indication of the amount of that component present in original sample introduced into the gas chromatograph.

In certain applications it has been found advantageous to provide the ion mobility spectrometer with a common unidirectional drift and source gas flow in order that all gas flows in the spectrometer may be vented at the inlet end downstream of the ionisation source 10. This has been found to have the effect of seriously impairing the sensitivity of the ion mobility spectrometer, possibly as a result of the incoming separated samples from the chromatograph being at least in part swept out of the source region prior to ionisation.

It is an object of the present invention to overcome or mitigate this reduction in sensitivity in an ion mobility spectrometer employing an inlet end exhaust venting arrangement with a unidirectional drift and source gas flow.

In order to achieve the object of the invention means are provided to prevent or minimise removal of the gas chromatograph effluent from the source region of the ion mobility spectrometer prior to ionisation.

According to one aspect of the invention, the effluent from the gas chromatograph is introduced together with a further gas flow into the ion mobility spectrometer in the region of the ionising source, in a direction counter to the flow of the drift and source gas.

According to a second aspect there is provided an ion mobility spectrometer having a unidirectional drift and source flow which is exhausted downstream of an ionisation source, and means for introducing into the spectrometer in the region of the ionisation source the effluent from a gas chromatograph together with a further gas flow, the effluent and the further gas flow being introduced in a direction counter to the said unidirectional drift and source flow.

The effluent and the further gas flow may be introduced into the ion mobility spectrometer with either one wholly or partly surrounding the other.

Preferably the effluent from the gas chromatograph is wholly or partly surrounded by the further gas flow.

For example the outlet from the gas chromatograph may be surrounded by a conduit through which the further gas flow passes, such that the two flows enter the ion mobility spectrometer together.

The gas chromatograph outlet and the conduit may be arranged substantially coaxially.

The further gas flow may have substantially the same velocity as, or a greater velocity than, the effluent from the gas chromatograph.

BRIEF DESCRIPTION OF THE DRAWINGS

This invention may be carried into practice in various ways and one specific embodiment will now be described, by way of example, with reference to the drawings, in which.

DESCRIPTION OF THE PREFERRED EMBODIMENTS

Figure 1:
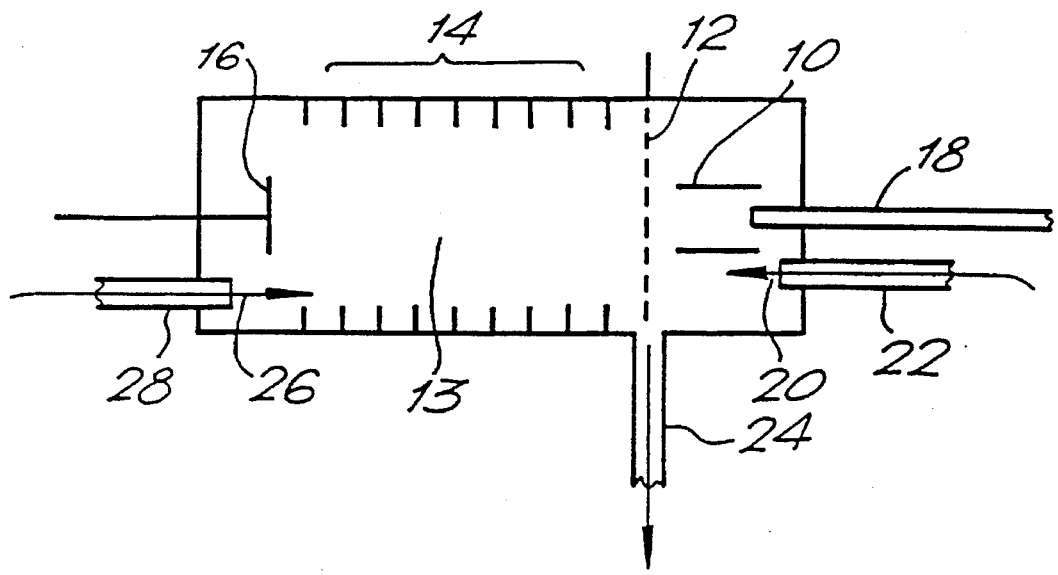
FIG. 1 is a diagrammatic illustration of part of a prior are gas chromatograph—IMS system.
Figure 2:
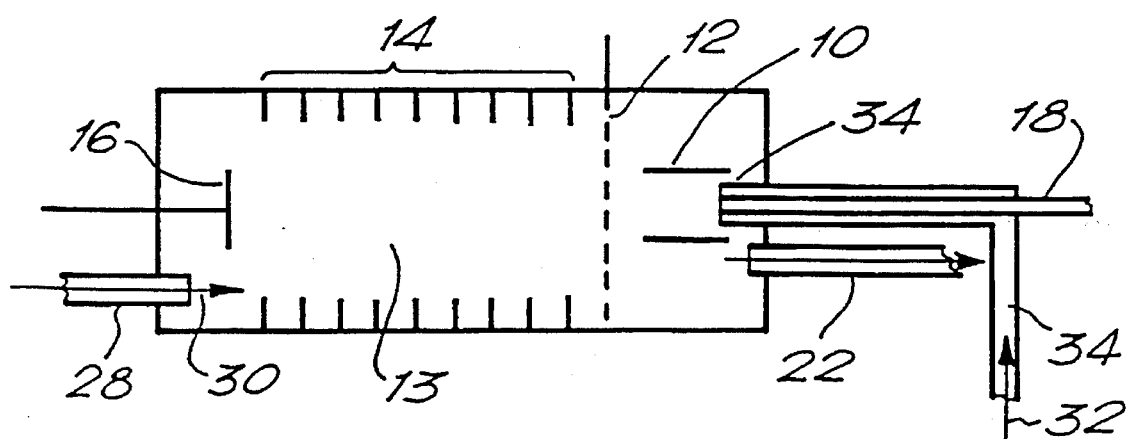
FIG. 2 is a diagrammatic illustration of part of a gas chromatograph—IMS system in accordance with an embodiment of the invention.

Referring to FIG. 2, in which similar parts bear the same reference numerals as in FIG. 1, a common unidirectional drift tube and source gas flow 30 is introduced into the drift tube 13 through the port 28. After traversing the drift tube 13 and the region of the ionising source 10, the combined gas flow 30 exhausts through the port 22.

Effluent from the gas chromatograph column outlet 18 is introduced into the region of the ionising source 10 surrounded by a further gas flow 32 introduced through a conduit 34 arranged about the outlet 18.

In the absence of the further gas flow it is believed that the effluent from the gas chromatograph, which has little momentum, meets the combined drift tube and source gas flow 30 moving through the source region and is swept back along the outer surface of the outlet 18 out of the ionisation region. This is believed to lead to poor ionisation efficiency for the emerging separated samples, poor ion extraction into drift tube 13 and hence a reduced sensitivity for the ion spectrometer.

One means of combatting the problem is to surround the incoming effluent with a surrounding gas flow moving in the same direction as the effluent, as described in relation to FIG. 2. The incoming effluent is thus not readily deflected or swept back by the gas flow 30, better mixing is achieved in the source region, giving improved ionisation efficiency, ion extraction and thus instrumental sensitivity.

It has been found by experiment that the best results are obtained when the further gas flow 32 moves with substantially the same or with a greater velocity than the chromatograph effluent, although the invention is not to be regarded as being thereby limited.

The further gas flow 32, and the combined drift tube and source gas flow 30, are conveniently both dry air.

It will be apparent that the invention is not limited to the embodiments described above and that variations and modifications may be made thereto within the scope of the invention.

I claim:

1. An ion mobility spectrometer having a drift area and a source area, a first unidirectional gas flow common to the said areas and exciting the spectrometer from the source area downstream of an ionization source, characterized by means for introducing into the source area in the region of the ionization source the effluent from the gas chromatograph together with a further gas flow, the further gas flow being introduced in a direction counter to that of the first gas flow, and the further gas flow wholly or partly surrounding the effluent, substantially without mixing, to sheathe the effluent.

2. An ion mobility spectrometer as claimed in claim 1 in which one of the effluent or the further gas flow enters the spectrometer through an opening, and the other of the effluent or the further gas flow enters through an annular opening which surrounds the said opening.

3. An ion mobility spectrometer as claimed in claim 2 in which the annular opening is substantially coaxial of said opening.

4. An ion mobility spectrometer as claimed in any one of the preceding claims in which, in use, the further gas flow has substantially the same velocity as, or a greater velocity than, the effluent.

5. An ion mobility spectrometer of claim 1 wherein the effluent, on entering the spectrometer, is entrained in the further gas flow.

* * * * *